United States Patent
Engelhard

(10) Patent No.: US 10,449,265 B2
(45) Date of Patent: Oct. 22, 2019

(54) HIGH EFFICIENCY ULTRA-VIOLET REACTOR

(71) Applicant: Rolf Engelhard, Prescott, AZ (US)

(72) Inventor: Rolf Engelhard, Prescott, AZ (US)

(73) Assignee: Blutec, LLC., Las Vegas, NV (US)

( * ) Notice: Subject to any disclaimer, the term of this patent is extended or adjusted under 35 U.S.C. 154(b) by 0 days.

(21) Appl. No.: 15/119,273

(22) PCT Filed: Feb. 18, 2015

(86) PCT No.: PCT/US2015/016438
§ 371 (c)(1),
(2) Date: Aug. 16, 2016

(87) PCT Pub. No.: WO2015/126982
PCT Pub. Date: Aug. 27, 2015

(65) Prior Publication Data
US 2017/0007736 A1  Jan. 12, 2017

Related U.S. Application Data

(60) Provisional application No. 61/941,398, filed on Feb. 18, 2014.

(51) Int. Cl.
*F24F 3/16* (2006.01)
*A61L 9/20* (2006.01)

(52) U.S. Cl.
CPC .............. *A61L 9/20* (2013.01); *A61L 9/205* (2013.01); *F24F 3/166* (2013.01); *F24F 2003/1667* (2013.01)

(58) Field of Classification Search
CPC .... A61L 9/20; A61L 9/205; F24F 3/16; F24F 2003/1667
See application file for complete search history.

(56) References Cited

U.S. PATENT DOCUMENTS

D48,392 S     1/1916 Loheide
2,255,491 A   9/1941 Mohen
(Continued)

FOREIGN PATENT DOCUMENTS

CN    002531297 Y   1/2003
CN    2664666 Y    12/2004
(Continued)

OTHER PUBLICATIONS

English Translation of JP 2004049468A Provided by the European Patent Office: Kondo, Chikahiko; Air Cleaner, Feb. 19, 2004.*
(Continued)

*Primary Examiner* — Kevin Joyner
(74) *Attorney, Agent, or Firm* — Mintz Levin Cohn Ferris Glovsky and Popeo, P.C.

(57) ABSTRACT

A high efficiency ultra-violet air purification system is disclosed. The system includes an apparatus for purifying air. The apparatus includes a chamber having a hollow interior and having an inlet and an outlet, the chamber having an inner reflective surface. The apparatus further includes an ultraviolet (UV) light source mounted within the hollow interior of the chamber between the inlet and the outlet. The apparatus further includes a honeycomb structure mounted to each of the inlet and the outlet of the UV chamber, the honeycomb structure having an array of hexagonal passages that are orthogonal to the inner reflective surface of the chamber, each hexagonal passage being at least partly coated with a UV catalyst and a UV light absorption coating.

19 Claims, 9 Drawing Sheets

(56) References Cited

U.S. PATENT DOCUMENTS

| | | |
|---|---|---|
| 2,738,224 A | 3/1956 | Checkovich et al. |
| 4,422,824 A | 12/1983 | Eisenhardt, Jr. |
| 5,680,016 A | 10/1997 | Valcke |
| D398,044 S | 9/1998 | Gutmann |
| 5,833,740 A | 11/1998 | Brais |
| 6,063,343 A | 5/2000 | Say et al. |
| D433,494 S | 11/2000 | Pinchuk et al. |
| 6,303,087 B1 | 10/2001 | Wedekamp |
| 6,365,113 B1 | 4/2002 | Roberts |
| D461,004 S | 7/2002 | Searle |
| D491,654 S | 6/2004 | Gatchell et al. |
| D495,043 S | 8/2004 | Gatchell et al. |
| D496,096 S | 9/2004 | Wang et al. |
| D501,248 S | 1/2005 | Chi-Hsiang et al. |
| 6,939,397 B2 | 9/2005 | Nelsen et al. |
| D513,797 S | 1/2006 | Wang |
| D522,116 S | 5/2006 | Zhixiang |
| D539,406 S | 3/2007 | Wang |
| D540,453 S | 4/2007 | Wang |
| D545,951 S | 7/2007 | Bucher et al. |
| D574,475 S | 8/2008 | Spiegel |
| D582,024 S | 12/2008 | Gao |
| D586,899 S | 2/2009 | Searle |
| D588,686 S | 3/2009 | Spiegel |
| D594,947 S | 6/2009 | Lewis |
| D603,949 S | 11/2009 | Campbell et al. |
| 7,674,436 B1 | 3/2010 | Feldman et al. |
| 7,695,675 B2 | 4/2010 | Kaiser et al. |
| D638,923 S | 5/2011 | Choi |
| D639,919 S | 6/2011 | Yu |
| 7,972,564 B2 | 7/2011 | Chan |
| 8,017,073 B2 | 9/2011 | Engelhard |
| D658,752 S | 5/2012 | Farone |
| 8,277,735 B2 | 10/2012 | Engelhard |
| D675,303 S | 1/2013 | Raupach et al. |
| D678,493 S | 3/2013 | Lacotta et al. |
| D678,992 S | 3/2013 | Choi |
| D683,006 S | 5/2013 | Spiegel |
| D683,007 S | 5/2013 | Spiegel |
| D691,255 S | 10/2013 | Abbondanzio et al. |
| D703,804 S | 4/2014 | Nuzzi, Jr. |
| D705,410 S | 5/2014 | Terao |
| 8,734,724 B2 | 5/2014 | Engelhard |
| D714,923 S | 10/2014 | Engelhard et al. |
| D731,633 S | 6/2015 | Farone et al. |
| 9,402,931 B2 | 8/2016 | Engelhard |
| 2002/0098127 A1 | 7/2002 | Bollini |
| 2002/0172627 A1 | 11/2002 | Aoyagi |
| 2003/0143133 A1 | 7/2003 | Liu |
| 2003/0155524 A1 | 8/2003 | McDonald et al. |
| 2003/0230477 A1 | 12/2003 | Fink et al. |
| 2004/0166018 A1 | 8/2004 | Clark et al. |
| 2005/0191219 A1 | 9/2005 | Uslenghi et al. |
| 2006/0057020 A1 | 3/2006 | Tufo |
| 2007/0041882 A1 | 2/2007 | Roseberry et al. |
| 2007/0207722 A1 | 9/2007 | McLeod |
| 2008/0014111 A1 | 1/2008 | Hedman |
| 2008/0048541 A1 | 2/2008 | Sumrall et al. |
| 2008/0112845 A1 | 5/2008 | Dunn et al. |
| 2008/0213129 A1 | 9/2008 | van der Pol et al. |
| 2009/0066257 A1 | 3/2009 | Kominami et al. |
| 2009/0285727 A1 | 11/2009 | Levy |
| 2010/0003164 A1 | 1/2010 | Bourne et al. |
| 2010/0143205 A1 | 6/2010 | Engelhard |
| 2012/0183443 A1 | 7/2012 | Hurley |
| 2014/0091236 A1* | 4/2014 | Jhawar ............... C02F 1/32 250/492.1 |
| 2016/0041074 A1 | 2/2016 | Pliskin |
| 2017/0067659 A1 | 3/2017 | Silver et al. |

FOREIGN PATENT DOCUMENTS

| | | | |
|---|---|---|---|
| CN | 1834542 A | | 9/2006 |
| EP | 1600201 A1 | | 11/2005 |
| JP | 09135891 A | * | 5/1997 |
| JP | H09135891 A | | 5/1997 |
| JP | 2002-174444 A | | 6/2002 |
| JP | 2002-178745 A | | 6/2002 |
| JP | 2004-036912 A | | 2/2004 |
| JP | 2004049468 A | * | 2/2004 |
| JP | 2004-069129 A | | 3/2004 |
| JP | 2005-161022 A | | 6/2005 |
| JP | 2005-164069 A | | 6/2005 |
| JP | 003110098 U | | 6/2005 |
| JP | 2008-116139 A | | 5/2008 |
| JP | 2009-538410 A | | 11/2009 |
| WO | WO-2007/142907 A1 | | 12/2007 |
| WO | WO-2008/117962 A1 | | 10/2008 |

OTHER PUBLICATIONS

English Translation of Japanese Document No. JP 09135891 provided by the European Patent Office espacenet.com: Makoto, Yumino; Takashi, Ando; Izumi, Saito; Deodorizing Device; Nov. 14, 1995 (Year: 1995).*

International Search Report Issued in PCT/US2015/016438 dated Jun. 1, 2015.

* cited by examiner

HIGH EFFICIENCY ULTRA-VIOLET REACTOR

CROSS-REFERENCE TO RELATED APPLICATION

This application is a national stage entry, filed under 35 U.S.C. § 371, of International Application No. PCT/US2015/016438, filed Feb. 18, 2015, and claims the benefit of and priority to U.S. Provisional Patent Application No. 61/941,398, filed Feb. 18, 2014, the entire content of which is hereby incorporated herein by reference in its entirety and for all purposes.

BACKGROUND

Ultraviolet (UV) light is well known for its ability to destroy microorganisms. Certain wavelengths of UV light in the UV-C spectrum are very effective in destroying bacteria, viruses, mold spores, protozoa, etc. Many of these organisms can be airborne and are hazardous to human health. As such, UV light in the germicidal range is well suited for purifying air that humans breathe. Many air purification systems are on the international market that incorporate a UV light for this purpose.

UV light in the UV-C spectrum is not visible to the human eye. However, exposure to UV-C light even in small doses and for short periods of time is harmful to the health of human beings and animals. Specifically, eyes and skin will be damaged when exposed to UV-C light. This is also true to a lesser degree for exposure to the UV light in the UV-A and UV-B range. Furthermore, UV light negatively affects the integrity of many different materials, especially plastics. As such, UV compatibility of materials is an important part of the design and construction of any device that produces UV light. Furthermore, any device that incorporates UV light must be designed in such a way that no UV light can escape and endanger the health of humans and animals.

Some conventional UV air purification applications consist of a UV reaction chamber, which has high intensity UV light inside and a method to move the air to be purified through this reaction chamber. Typically, this is done with some sort of a fan, compressor, or in some cases, convection flow. The overall UV intensity within that UV reaction chamber determines how long the air must remain in this chamber in order to reduce harmful microbes that are present in the air to a desired level. For instance, in a very high UV intensity chamber, airborne viruses may require an exposure of 1 second for a 99.9% reduction. In a lower intensity environment, the exposure may require several seconds to achieve the same reduction.

A typical UV air purifier would include A UV reaction chamber through which the air flows. This chamber often times is cylindrical but can also be a cube or other shape. This chamber can be made of a material that is somewhat UV reflective, which will increase the overall UV dose. As an alternate, the UV chamber can be coated with a reflective material.

Inside the UV reaction chamber is a UV light source. Typically, this would be a low-pressure mercury vapor lamp designed to generate UV light in the germicidal range. These lamps can be made in a number of different shapes, but the most common are straight tubular lamps or variations in which the tube is twisted into different shapes. Such a design could be a U lamp where the tube is twisted into a U shape, or a spiral design where the tube is twisted into a spiral shape. UV reaction chambers also include a fan or other air moving mechanism that blows the air to be purified through the UV reaction chamber where it is exposed to UV light.

A design where air needs to flow through a UV reactor chamber presents a number of challenges. First, the air needs to flow freely through the chamber where it is being exposed to ultra-violet light. The chamber needs to be designed in such a way that there is very little restriction to airflow. Ideally, a chamber such as a cylindrical chamber would have to be opened on both ends so a relatively small fan can freely move the air through the cylinder at a relatively high flow rate.

Second, the chamber needs to be designed in such a way that no UV light exits the chamber in order to prevent damage to eyes, skin and construction materials such as plastics. Such a design would generally require a UV light barrier on the inlet and outlet side of the UV chamber. In order for the barrier to be effective, it would have to create a rather tortuous path for the light to travel before the light reaches the outside. In the tortuous path, the barrier would have to absorb the UV light to prevent it from exiting.

The above two criteria appear to work against each other. A design that creates a tortuous path for the UV light also creates a tortuous path for the airflow. As such, a good UV light barrier becomes a great restrictor for airflow requiring larger fans, which by their nature create more noise. For an application such as a residential air purifier, conventional methods have proven to be unsuitable because the large fan requirements for overcoming the high airflow restrictions create unacceptable noise levels.

SUMMARY

A high efficiency, ultra-violet (UV) air purification system, apparatus, and method are disclosed. A system includes an apparatus for purifying air. The apparatus includes a chamber having a hollow interior and having an inlet and an outlet, the chamber having an inner reflective surface. The apparatus further includes an ultraviolet (UV) light source mounted within the hollow interior of the chamber between the inlet and the outlet. The apparatus further includes a honeycomb structure mounted to each of the inlet and the outlet of the UV chamber. The honeycomb structure has an array of hexagonal passages that are orthogonal to the inner reflective surface of the chamber, each hexagonal passage being at least partly coated with a UV catalyst and a UV light absorption coating.

In another aspect, an apparatus include a chamber having a proximal opening and a distal opening, and an ultraviolet (UV) light source mounted within the chamber between the proximal opening and the distal opening. The apparatus further includes a UV light absorbing member coupled to each end of the UV light source near the proximal opening and the distal opening of the chamber.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This document describes a high-efficiency UV reactor that can be used, among various applications, in a high-intensity air purifier (HIAP), such as those described in U.S. patent application Ser. No. 12/628,180, entitled "High Intensity Air Purifier" and the contents of which are incorporated by reference herein for all purposes.

The high-efficiency UV reactor is a solution to all the above problems in addition to other benefits. The high-efficiency UV reactor creates a virtually wide-open airflow with no restriction, and yet eliminates any harmful UV exposure to a person looking into the reactor. Prototypes have been built and tested, both for their airflow characteristics and their ability to absorb UV light.

Figure 1:
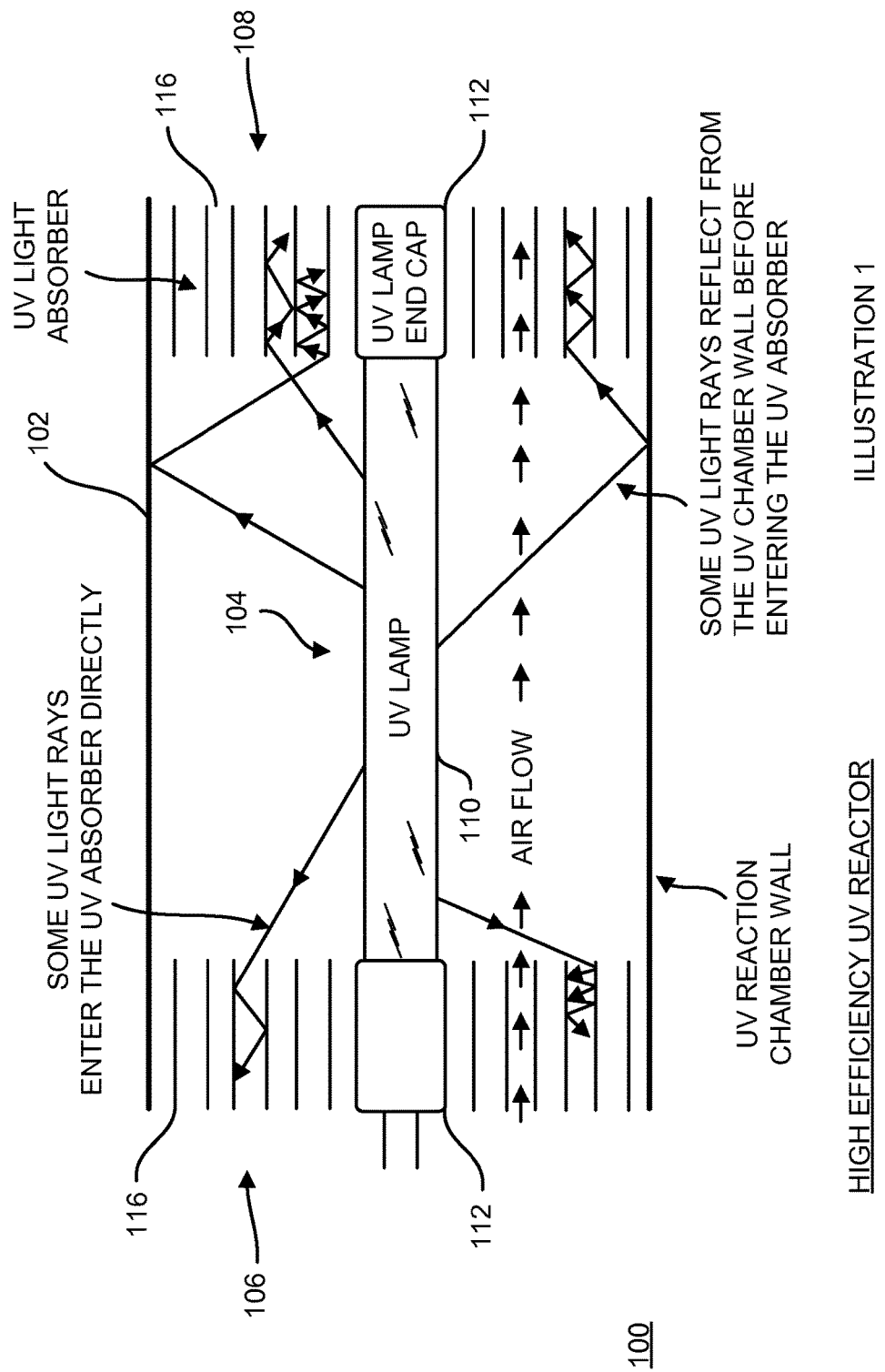
FIG. 1 illustrates a high-efficiency UV reactor, in accordance with implementations described herein.

In some implementations, as shown in FIG. 1, a high-efficiency UV reactor 100 includes a substantially hollow UV chamber 102 that has an inlet 106 and an outlet 108, with a straight UV lamp 104 mounted inside of the UV chamber 102. In some implementations, the UV chamber 102 is cylindrical, and the UV lamp 104 is mounted in the center of UV chamber 102, although the UV chamber 102 can have any shape and/or cross-section, and the UV lamp 104 can be mounted in any position or orientation within the UV chamber 102. In some implementations, the UV chamber 102 includes the UV lamp 104 within a tube formed by the UV chamber 102. The tube of the UV chamber 102 can include aluminum, as aluminum is a fairly good reflector of UV light. As such, a portion of the UV light that strikes the UV chamber 102 is reflected inward rather than being absorbed by the wall of the UV chamber 102

There are some basic differences between UV-C light and visible light. UV-C light has a higher frequency and shorter wavelengths than visible light. UV-C is not visible to the human eye, so when a person looks into a UV-C light source, the light seen is not in the UV-C spectrum, but rather in the visible spectrum. One major difference between UV-C and visible light is its reflectivity. Most materials and surfaces that readily reflect visible light reflect very little UV-C light. For instance, a common mirror that we use daily reflects nearly 100% of visible light yet it absorbs nearly 100% of UV-C light. Another example would be a white wall, which reflects mostly visible light yet virtually no UV-C light. The high absorption of UV-C light by most surfaces of the UV chamber 102 is a key to the success of the high-efficiency UV reactor 100.

Another aspect of the high-efficiency UV reactor 100 described herein is the pattern by which most UV-C lamps radiate UV-C light. Such as in the case of the HIAP described above, the UV lamp 104 is a tubular lamp that consists of a quartz body 110 from which UV-C light is generated, and a ceramic end cap 112 on each end of the lamp 104 that is opaque to UV light. The quartz body radiates UV-C light outwardly, while the end caps, which are constructed of an opaque material, do not transmit any light. As such, the lamp 104 emits light radially, not axially. In other words, light is emitted at a positive angle away from the longitudinal axis of the UV-C lamp. FIG. 1 illustrates how a light beam may actually travel within the UV chamber 102. As can be seen, some light travels directly from the UV lamp 104 to both the inlet 106 and the outlet 108 openings of the UV reaction chamber 102. Other light strikes the reflective wall of the UV chamber 102 and then travels to the inlet 106 or outlet 108 side of the UV chamber 102. Accordingly, all light that reaches the inlet 106 and/or outlet 108 of the UV reaction chamber 102 reaches it at an angle relative to the longitudinal centerline of the chamber 102. No light attempts to leave the chamber parallel to the centerline.

The inlet 106 and outlet 108 of the cylindrical UV chamber include a UV light absorber as a honeycomb structure 116. The honeycomb structure 116 has a large number of very small passages. Due to the nature of the honeycomb, these passages are hexagonal in shape. As indicated in FIG. 1, all light that strikes this honeycomb disc does so at an angle. As such, no light can travel through the honeycomb in a straight line without touching or bouncing off the walls of the passages, or cells, of the honeycomb structure 116. Light rays have to bounce through each honeycomb cell several times before they can exit. In order words, light rays are reflected off the walls of each honeycomb cell several times before exiting the cell.

In some implementations, as shown in FIGS. 2-9, a honeycomb structure made of natural aluminum is used. In a preferred exemplary implementation, the cell size is approximately 1 mm, but can have a cross-sectional diameter or spacing of between 0.5 to 2mm or more. Assuming that natural aluminum reflects 90% of visible light, but only 30% of UV-C light. This would mean that as light "bounces" through a honeycomb cell, 70% of all UV-C light is absorbed with each reflection by the aluminum and 10% of all visible light. Further, in a given cell, a light ray can be reflected four or more times, only 1% of the UV-C light will actually exit the chamber since with each reflection, and 70% of the UV-C light is absorbed by the aluminum. Further, black anodizing dramatically reduces the reflectivity of aluminum. Therefore, in the example mentioned, a black anodized honeycomb structure absorbs the majority of the UV-C light to a point where it no longer presents a danger to eye or skin and is no longer destructive to plastic materials. As can be seen, visible light still exits the UV chamber since the aluminum honeycomb only absorbs a small portion of it. Furthermore, the honeycomb used and shown has an open area of more than 90%, which presents an insignificant resistance to open airflow allowing the use of a small quiet fan.

In some implementations, a black anodized aluminum honeycomb structure is used, since it is readily available on the market. However, any material that is resistant and absorbs a large portion of UV-C light can be used. Also, the individual cells do not have to be hexagonal; they can be round, square, rectangular, triangular or any other shape. They could even be a series of individual tubes or rods. Of importance is the size of the cells. The smaller and longer the cell, the more often the light has to be reflected, and consequently the more UV-C light is absorbed.

The UV light absorber has applications wherever air needs to be moved through a UV reaction chamber and UV light has to be retained within this chamber. Other shapes of lamps can be used as long as they do not radiate light longitudinally within the chamber. In the case of U lamps, H lamps, spiral lamps, spherical lamps, a shield would have to be incorporated on two sides of a lamp, which would serve the same purpose of the end caps in a tubular UV lamp.

FIGS. 2-9 show a funnel connected to the aluminum honeycomb, which can be incorporated in production air purifiers for the purpose of guiding the UV lamp through the chamber during installation. Since the UV reactor chamber is a solid enclosure, the consumer would have difficulty replacing the lamp without this funnel that will naturally guide and center the lamp through the honeycomb.

A honeycomb structure has a very large surface area. Because of this, honeycombs can be used as a substrate for a catalyst. Such catalysts can be applied for the reduction of chemical and microbial compounds. Such catalysts can include the following: manganese dioxide converts ozone into oxygen. Platinum-based catalysts convert ozone into oxygen and carbon monoxide into carbon dioxide.

Photo catalysts are a new family of catalysts that have emerged in recent years. Photo catalysts such as titanium dioxide require UV-A, B or C irradiation to be activated. When irradiated with ultra-violet light, a photo catalytic coating will generate hydroxyl radicals, which will very affectively oxidize microbial and chemical compounds. In some implementations, a photo catalytically coated honeycomb will not only absorb the UV light but add this additional benefit.

Figure 2:
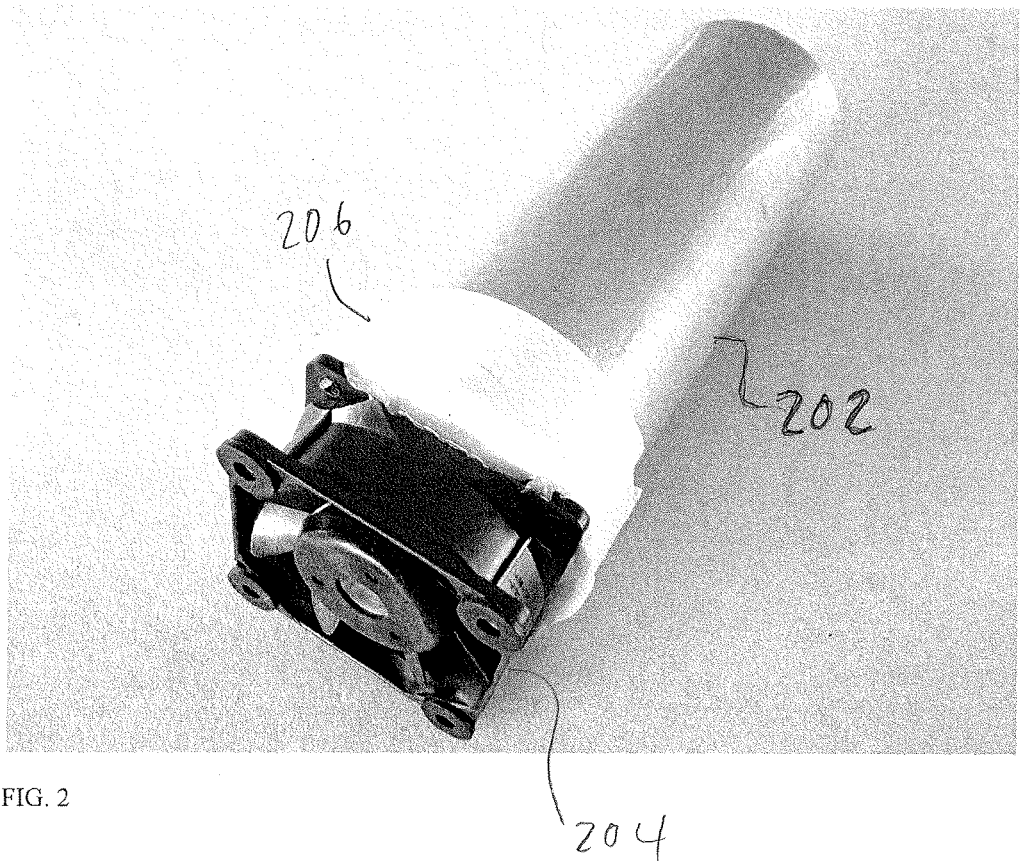
FIG. 2 shows a UV reactor and fan attached to one end of the reactor chamber.
Figure 3:
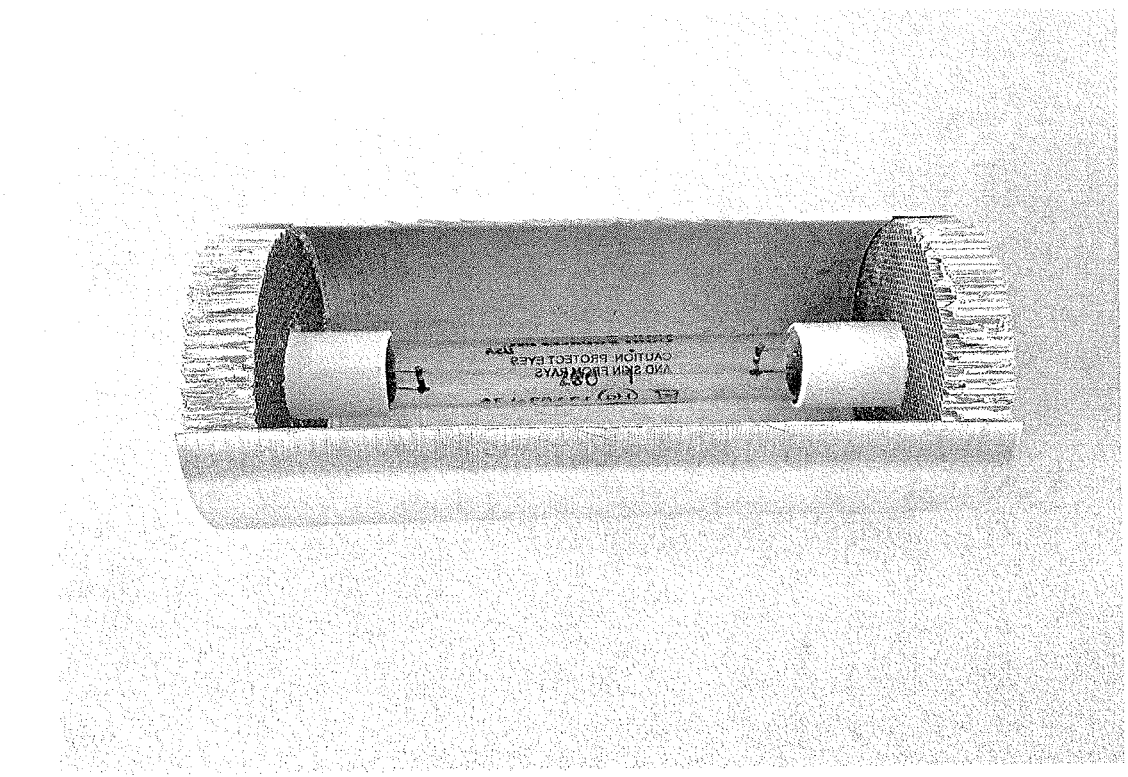
FIG. 3 is a cutaway view of a UV reactor chamber.
Figure 4:
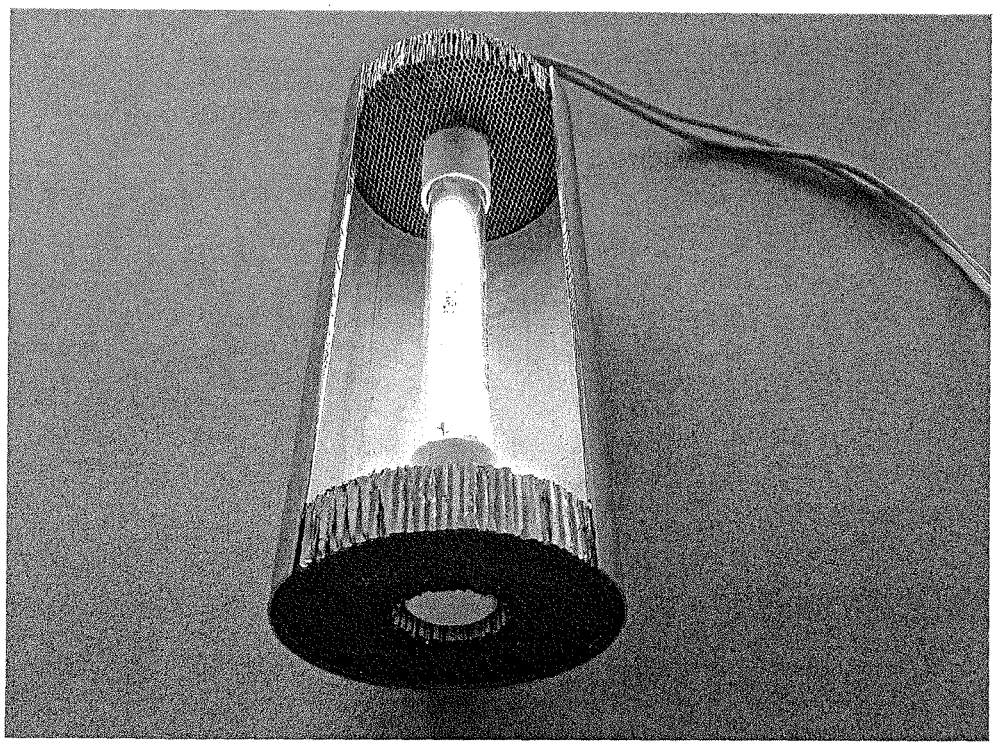
FIG. 4 is a cutaway view of the UV reactor chamber with the UV source activated.
Figure 5:
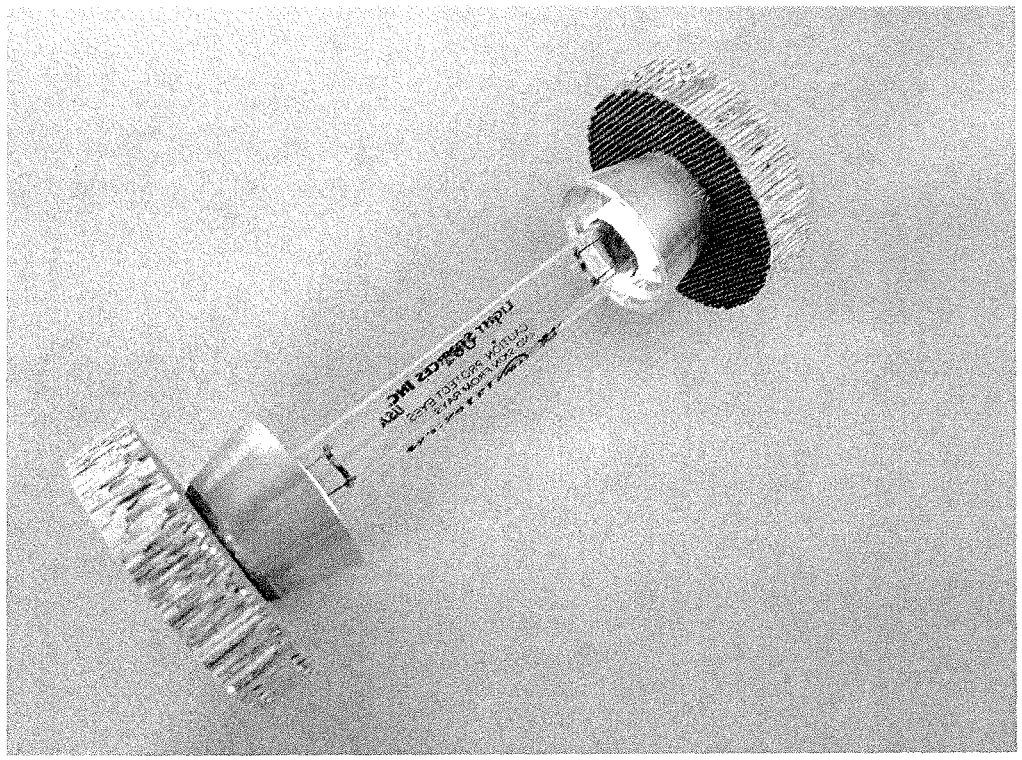
FIG. 5 shows the UV source and honeycomb funnels connected at either end of the UV source to shield a user from direct UV light.
Figure 6:
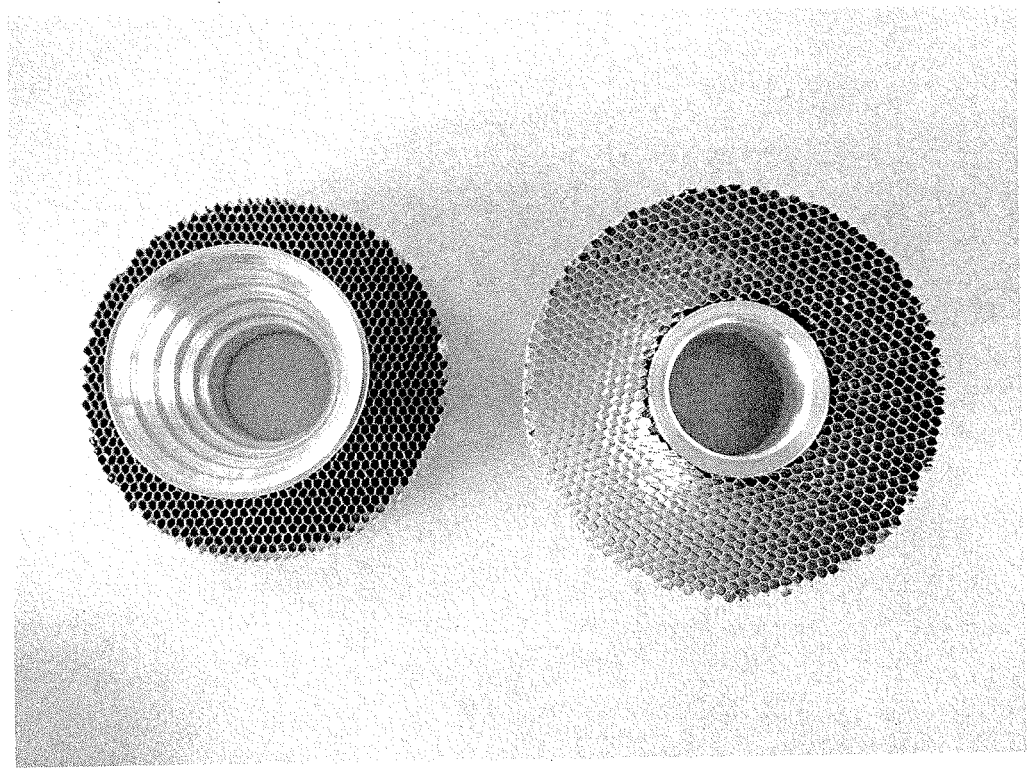
FIG. 6 shows top-down views of the honeycomb funnels.
Figure 7:
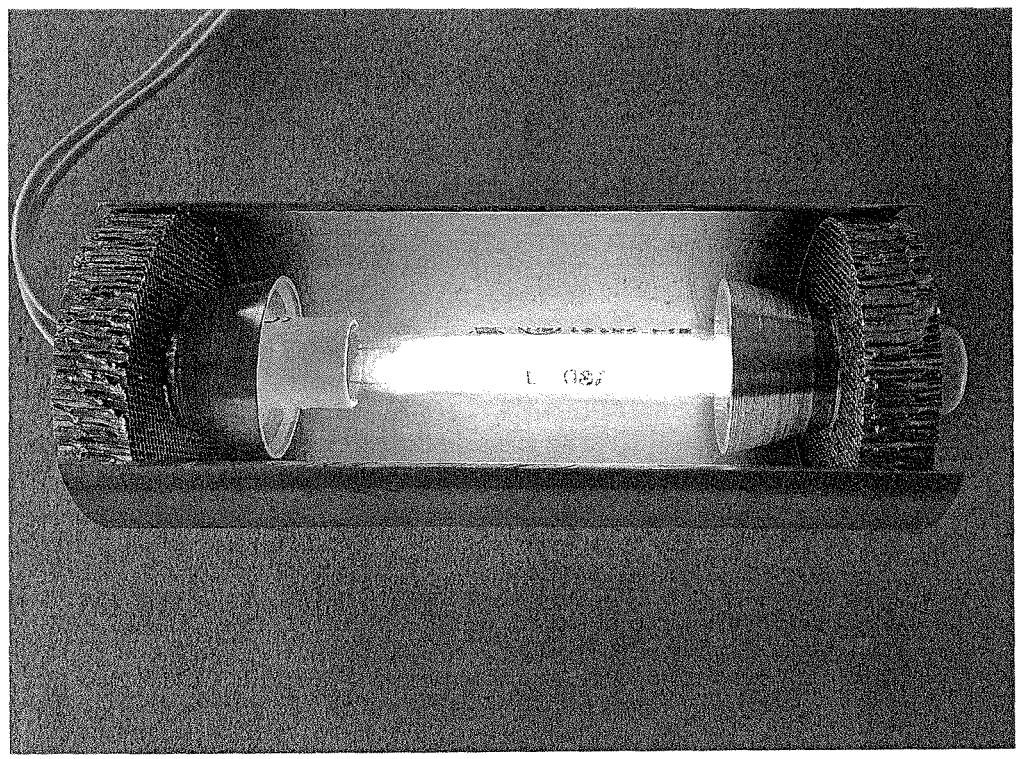
FIG. 7 is a cutaway view of the UV reactor chamber and honeycomb funnels, with the UV source activated.
Figure 8:
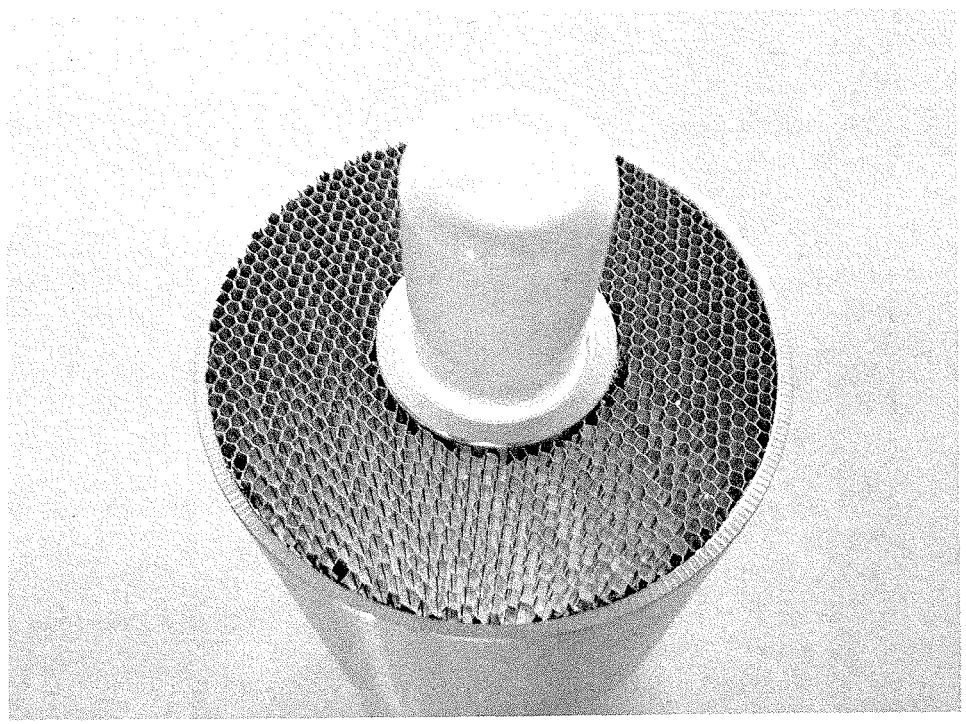
FIG. 8 shows a top-down view of a honeycomb funnel with a UV source activated underneath.
Figure 9:
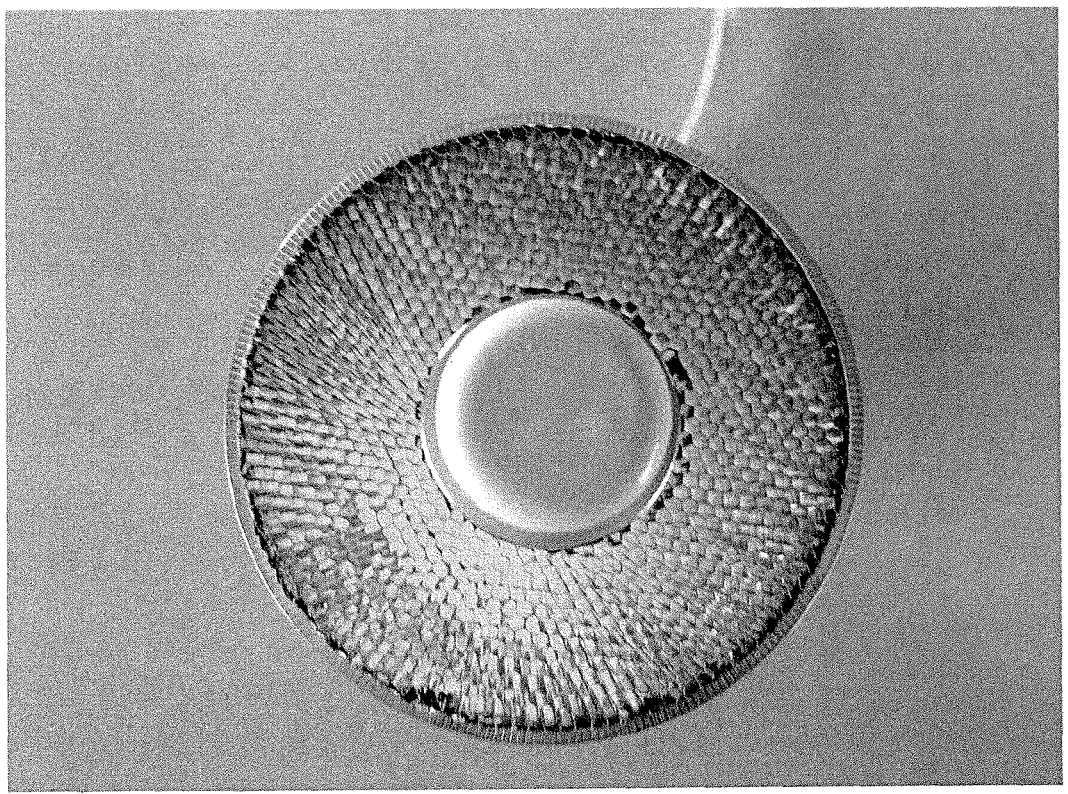
FIG. 9 is an alternative view of a top-down view of a honeycomb funnel with a UV source activated underneath.

In some implementations, a UV reaction chamber 202 as described above can be combined with an axial fan 204, as shown in FIG. 2. Axial fans by themselves have a design drawback in the fact that they do not move air in a linear axial fashion. Instead, while they do push the air forward due to the deflection of the angled fan blades, they also rotate the air spirally with the direction of the fan blade rotation. As such, a portion of the fan motor's energy is used to rotate the air rather than pushing the air forward. A honeycomb structure 206, on the other hand, will only allow linear airflow through its individual cells. Therefore, attaching a honeycomb structure to the outlet side of an axial fan, as shown, forces the air from the axial fan to flow in a linear axial direction. This actually increases the efficiency of an axial fan 204. Accordingly, the addition of a honeycomb structure 206 creates the synergistic effect of serving as a UV light absorber, an airflow director and potentially a catalyst.

Although a few embodiments have been described in detail above, other modifications are possible. Other embodiments may be within the scope of the following claims.

The invention claimed is:

1. An apparatus comprising:
a chamber having a proximal opening and a distal opening;
an ultraviolet (UV) light source mounted within a center of the chamber and between the proximal opening and the distal opening; and
a UV light absorbing member coupled to each end of the UV light source near the proximal opening and the distal opening of the chamber, the UV light absorbing member including a black anodized aluminum honeycomb structure.

2. The apparatus in accordance with claim 1, wherein the black anodized aluminum honeycomb structure includes an array of passages that are coated with a UV catalyst.

3. The apparatus in accordance with claim 2, wherein each passage of the array of passages has a cross-sectional diameter of 0.5 to 2 mm.

4. The apparatus in accordance with claim 3, further comprising an axial fan for causing air to flow through the chamber, the black anodized aluminum honeycomb structure being attached to an outlet side of the axial fan and directing air from the axial fan in a linear axial direction.

5. The apparatus in accordance with claim 1, wherein the UV light source includes a quartz lamp to generate UV-C light, and an opaque end cap on each end of the quartz lamp.

6. The apparatus in accordance with claim 5, wherein the opaque end cap of the UV light source is formed of ceramic.

7. The apparatus in accordance with claim 1, wherein the chamber is cylindrical and the UV light source is mounted within the center of the chamber such that the UV light source extends along a longitudinal axis of the chamber.

8. An apparatus comprising:
an ultraviolet (UV) chamber having an inlet and an outlet, the UV chamber being coated with a reflective material;
a UV light source mounted within a center of the UV chamber and between the inlet and the outlet; and
a black anodized aluminum honeycomb structure mounted to each of the inlet and the outlet of the UV chamber, the black anodized aluminum honeycomb structure having an array of hexagonal passages, each hexagonal passage being at least partly coated with a UV catalyst.

9. The apparatus in accordance with claim 8, wherein each hexagonal passage has a maximum cross-sectional diameter of 0.5 to 2 mm.

10. The apparatus in accordance with claim 8, wherein the UV light source includes a quartz lamp to generate UV-C light, and an opaque end cap on each end of the quartz lamp.

11. The apparatus in accordance with claim 10, wherein the opaque end cap of the UV light source is formed of ceramic.

12. The apparatus in accordance with claim 8, further comprising a fan mounted at the outlet of the UV chamber, the fan being adapted to pull air into the inlet, through the UV chamber, and out through the outlet.

13. The apparatus in accordance with claim 8, wherein the UV light source is mounted within the center of the chamber such that the UV light source extends along a longitudinal axis of the chamber.

14. An apparatus comprising:
a chamber having a hollow interior and having an inlet and an outlet, the chamber having an inner reflective surface;
an ultraviolet (UV) light source mounted within a center of the hollow interior of the chamber and between the inlet and the outlet; and
a black anodized aluminum honeycomb structure mounted to each of the inlet and the outlet of a UV chamber, the black anodized aluminum honeycomb structure having an array of hexagonal passages that extend parallel to the inner reflective surface of the chamber, each hexagonal passage being at least partly coated with a UV catalyst.

15. The apparatus in accordance with claim 14, wherein each hexagonal passage has a maximum cross-sectional diameter of 0.5 to 2 mm.

16. The apparatus in accordance with claim 15, further comprising an axial fan for causing air to flow through the chamber, the black anodized aluminum honeycomb structure being attached to an outlet side of the axial fan and directing air from the axial fan in a linear axial direction.

17. The apparatus in accordance with claim 14, wherein the UV light source includes a quartz lamp to generate UV-C light, and an opaque end cap on each end of the quartz lamp.

18. The apparatus in accordance with claim 17, wherein the opaque end cap of the UV light source is formed of ceramic.

19. The apparatus in accordance with claim 14, further comprising a fan mounted at the outlet of the chamber, the fan being adapted to pull air into the inlet, through the hollow interior of the chamber, and out through the outlet.

* * * * *